United States Patent [19]
Hollandsworth

[11] Patent Number: 5,878,380
[45] Date of Patent: Mar. 2, 1999

US005878380A

[54] METHOD AND APPARATUS FOR ULTRASOUND BLOCK MEASUREMENT

[76] Inventor: Paul R Hollandsworth, 3661 Mill Bridge Way, Chesapeake, Va. 23323

[21] Appl. No.: 747,063

[22] Filed: Nov. 8, 1996

Related U.S. Application Data

[60] Provisional application No. 60/007,334 Nov. 9, 1995.

[51] Int. Cl.⁶ .................................................. G01B 17/06
[52] U.S. Cl. ............................. 702/159; 702/171; 73/627; 73/628
[58] Field of Search ........................ 73/627, 628; 367/96, 367/99, 103, 104, 105, 140; 364/564, 567, 552, 560, 559; 702/39, 158, 159, 167, 171

[56] References Cited

U.S. PATENT DOCUMENTS

| | | |
|---|---|---|
| 4,305,294 | 12/1981 | Vasile . |
| 4,332,016 | 5/1982 | Berntsen ................................... 73/628 |
| 4,800,757 | 1/1989 | Hashinoki . |
| 4,841,489 | 6/1989 | Ozaki . |
| 4,866,614 | 9/1989 | Tam . |
| 4,873,651 | 10/1989 | Raviv ....................................... 364/513 |
| 4,887,246 | 12/1989 | Hossack et al. ......................... 367/140 |
| 4,945,501 | 7/1990 | Bell et al. ........................... 364/571.05 |
| 5,029,475 | 7/1991 | Kikuchi . |
| 5,042,015 | 8/1991 | Stringer ..................................... 367/99 |
| 5,062,297 | 11/1991 | Hashimoto . |
| 5,078,013 | 1/1992 | Kuramochi . |
| 5,105,392 | 4/1992 | Stringer et al. ........................... 367/99 |
| 5,113,358 | 5/1992 | Reber . |
| 5,125,273 | 6/1992 | Negita . |
| 5,220,536 | 6/1993 | Stringer et al. ........................... 367/99 |
| 5,220,839 | 6/1993 | Kibblewhite . |
| 5,351,543 | 10/1994 | Migliori . |
| 5,422,861 | 6/1995 | Stringer et al. ........................... 367/99 |
| 5,590,060 | 12/1996 | Granville et al. ....................... 364/560 |

*Primary Examiner*—Hezron Williams
*Assistant Examiner*—Rose M. Miller
*Attorney, Agent, or Firm*—John F. Carroll, IV; Eric M. Bram

[57] ABSTRACT

A method has been invented of providing feedback regarding tolerance for a dimension of a concrete block in relation to a datum in a computer-based system with a CPU, an input connected to the CPU, a memory associated with the CPU, a data transmitter connected to the CPU, a controller card connected to the data transmitter, an ultrasound transducer connected to the controller card, a timing device connected to the controller card, a memory means associated with the controller card, a feedback device connected to the controller card, and an environmental adaptator. Also, the invention can be described as an environmentally adaptable computer-based apparatus utilizing ultrasound for providing feedback regarding the dimensional quality of concrete blocks positioned on pallets traveling on a conveyor. The apparatus has a first memory for controlling a CPU, an input, an ultrasound transducer, a timing device, a second memory, a controller card, a data transmitter, a CPU, and a feedback device.

10 Claims, 2 Drawing Sheets

Microfiche Appendix Included
(3 Microfiche, 195 Pages)

METHOD AND APPARATUS FOR ULTRASOUND BLOCK MEASUREMENT

This application claims priority under 35 USC §119(e) to provisional application 60/007,334 filed Nov. 9, 1995.

This application contains three appendices on microfiche. The microfiche appendices are on three microfiche sheets with a total of 195 frames.

FIELD OF THE INVENTION

This invention relates generally to concrete masonry unit (cinder block) manufacture, and more specifically to automated measurement of cinder block height during the manufacturing process.

BACKGROUND AND SUMMARY OF THE INVENTION

The concrete industry for the past 35–40 years has not had very many improvements in the way they make cinder blocks. Some of the more prominent manufacturers of block forming equipment have been breaking ground in automation for the past several years but have not developed a calibration device for checking whether the cinder blocks are within tolerance; that is, $7\frac{5}{8} \pm \frac{1}{8}$". A currently used system has the blocks being manufactured at a variable rate of up to eight blocks every six seconds. Occasionally a worker will apply a metal template measuring $7\frac{5}{8}$" to check for height tolerance. This calibration inspection can be done when a cinder block is wet because there is very little shrinkage to consider. The equipment generally used for making cinder block can provide six different configurations, i.e., two 12-inch blocks, two 10-inch blocks, three 8-inch blocks, four 6-inch blocks, six 4-inch blocks, and eight 3-inch blocks, on each pallet.

Previous designs for mechanical solutions to the problems of assuring manufacture of blocks within tolerance did not overcome such obstacles as high Db noise levels, dirty environment, vibration, a fluctuating change in relative humidity, temperature, and wind gusts in the manufacturing environment. Some of these obstacles could not be solved with a standard engineering design. One attempt to solve the problems involved included a calibration device which mounted horizontally and attempted to overcome the difficulty in compensating for the calibration device for material buildup on the 22 by 26 inch steel plate. Over a period of a year, material build-up on the steel plate or pallet does affect the tolerances.

Avoiding preconceived ideas held by those working in the field, a method for solving this problem was discovered that the engineers had overlooked because of the built-in paradigms. A working model was developed and a prototype test was performed in October 1988 at a TARMAC Lone Star block manufacturing site. This test revealed that the device should be able to overcome the variable speed of the conveyor system, and should be shielded in case of an accident (e.g., kickback). The prototype calibration device proved very successful in this test. The particular device tested interfaced with a programmable logic controller, proximity sensor, and a marking device that would score the cinder blocks that were out of tolerance.

The plant where the alpha test was run produces 12 million blocks a year with about 3 percent in defects. The manufacturer loses money when he has to sell a cinder block as a second. As an example of the potential cost of cumulative errors in cinder block tolerance, one plant provided all the cinder blocks for the exterior and interior walls for a school built. Because the cinder blocks were $\frac{1}{8}$ inch out of tolerance, after eight tiers the wall was an inch out of line. The architect on the school site caught the mistake and required the replacement of 55,000 cinder blocks. This resulted in the entire section having to be torn down and rebuilt with new block. The cost was many thousands of dollars, and damage to the block manufacturer's reputation.

Additional capabilities that can be included in this calibration device include a counter that tells how many blocks are manufactured, and how many defects are found, having the device inform the worker that the block machine is out of tolerance and by how much, and for the device to shut off the block machine when it was producing cinder blocks out of tolerance.

In the plant environment tested, the production rate ranged from a slow 900 blocks to a fast 1500 blocks per hour per machine. The average speed at the block plant was approximately 1200 blocks per hour with two machines running concurrently.

In one embodiment of the present invention, if the sensing device measures a set of blocks that is out of tolerance, an audible alarm sounds and an LED display shows whether the tolerance was high or low and by how much, and at the same time the block is marked with a raking action. This concept was rejected for a preferred embodiment because marking a bad block only adds to the problem, and it makes better business sense to correct the problem immediately rather than incur the costs involved with manufacturing a bad block.

Accordingly, one object of the invention is to provide a calibration device and system that provides a combination of the following capabilities: Performing measurement tolerance to 0.015 inch, continuous self-calibration, simplified operational control, pallet tolerance, a supervisory control panel, data history, a visual and/or audio alarm, ruggedized construction, and multiple configuration measurement.

Another object of the invention is to provide the dual advantage of first, saving money for the customer by preventing the manufacturing of bad blocks, and second, improving the quality of the manufactured block worldwide.

Another object of the invention is to provide a system that can be installed quickly, with modular components, that provides low maintenance, that is very user friendly, and that can be utilized as part of new equipment or as a field add-on to existing units.

One of the features that has been designed into this product to overcome such obstacles as high Db noise levels, dirty environment, vibration, and a fluctuating change in relative humidity, temperature, and wind gusts, is a self-calibrating ultrasonic sensor.

An embodiment of the invention uses independently measuring ultrasonic sensors mounted vertically over a conveyor system. The sensors are adjustably placed so as to span the entire number of cinder blocks across the pallet on the conveyor system. The sensors take measurements of the heights of the cinder blocks and compare them to preset specification criteria. At the same time, the number of good and bad pallets manufactured is counted.

One embodiment of a system according to the present invention provides multiple measurements (100 measurements every 3 seconds) with each transducer, then computes an average and compares it to the plant's tolerance specification. All out-of-tolerance pallets are rejected. If three consecutive pallets are detected with height calculations that are out of tolerance, an alarm will sound, a strobe light will light and revolve, or a beeper will be activated, so that the block manufacturing machine can be adjusted. Alternatively, a signal may be sent to the pallet dumper when an out-of-tolerance pallet is detected, so that the blocks of that pallet may be destroyed and recycled for new block construction.

One embodiment of apparatus for operating the method of the invention comprises three elements—a bracket, which houses a controller circuit card operating a control and measurement algorithm of the method of the invention, signal generators, and transducers; a computer for providing overall control of the process, and a power panel with an attached strobe light. This apparatus can operate with different settings, and information on multiple configurations can be placed into and stored in memory.

The computer and accompanying software include WINDOWS capability and comprise a WINDOWS based monitor application that affords a graphical representation of what is calibrated and observed. If an alarm sounds, the monitor will show how much out tolerance and whether the equipment needs to be to be raised or lowered. Additionally, a 3 Dimensional model illustrates whether the out-of-specification tolerance was on the left, right or in the center. A control panel in a WINDOWS application running on a computer gives either a 3-Dimensional graphical representation, or actual measurement data detailing the out-of-tolerance condition so it can be corrected quickly.

An authorized user (a password can be set so that only a foreman or other authorized person can perform this function), can activate the tolerance setting and use either keyboard or mouse for setting display characteristics (e.g., whether to measure the distance from the transducers of all the ultrasonic sensors to the pallet in inches or in centimeters) or, if necessary, to activate the calibration routine which can automatically perform its own distance calibration. The user can also set the height that is required for the block, what tolerances are allowed, what type of alarm should be given, etc.

As an additional feature, the invention includes self-diagnostics, to pinpoint malfunctioning equipment in case of a transducer failure.

The control panel is ruggedized, so that it can be washed off with water with no ill effects. The strobe light is designed to be seen from far distances in fairly well-lit environments.

BRIEF DESCRIPTION OF THE DRAWING

For a fuller understanding of the nature and objects of the invention, reference should be made to the following description of a preferred mode of practicing the invention, read in connection with the accompanying drawing, in which.

DETAILED DESCRIPTION

Figure 1:
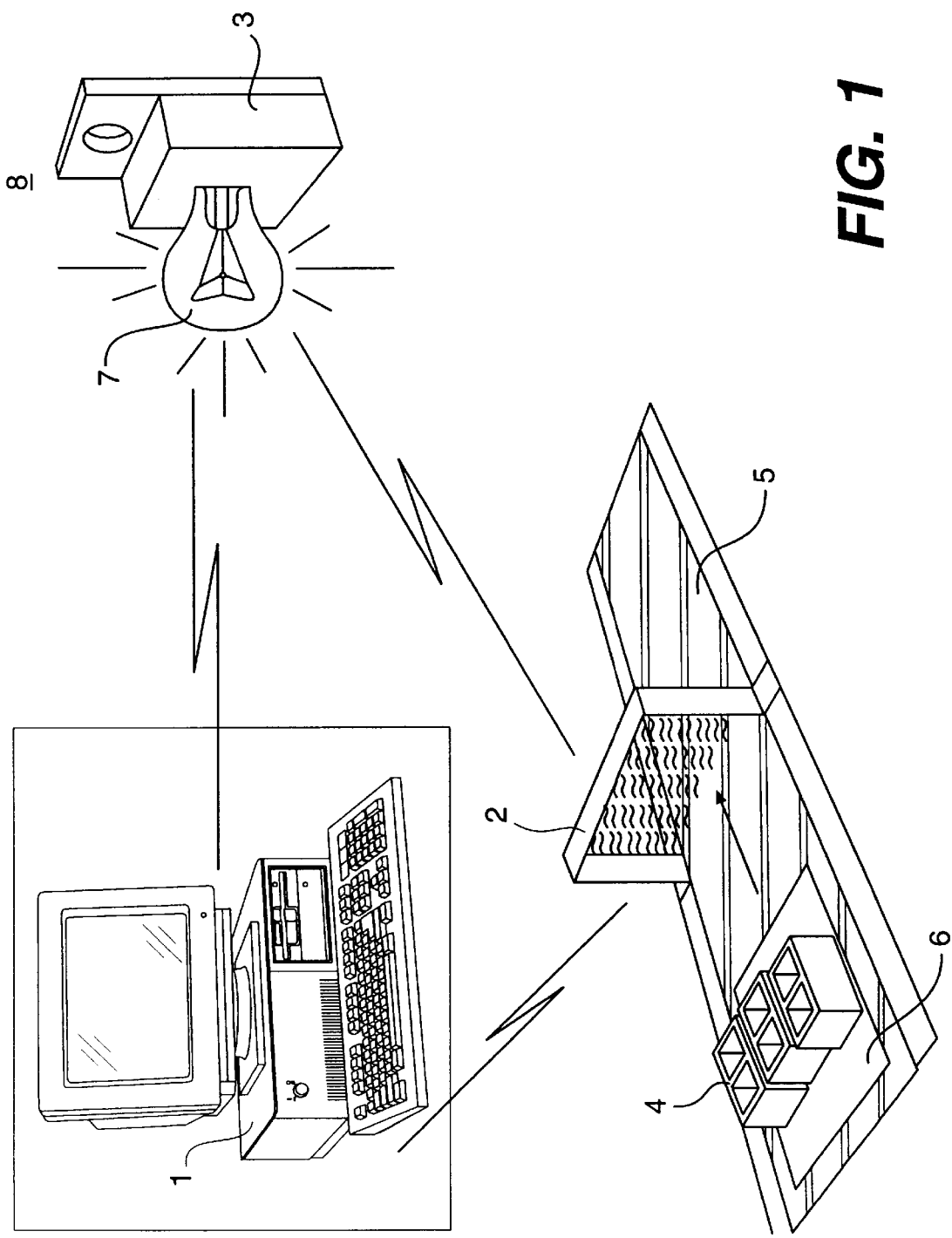
FIG. 1 is an overview perspective illustration of one embodiment of an apparatus for accomplishing the method of the invention.

An embodiment of the method and apparatus of the invention is now described. With reference to the drawing, a "personal computer" (PC) 1 with processor 9 allows the user to change various control conditions and measurement and testing criteria, and affords a graphical representation of what is calibrated and observed. The PC 1 is preferably located in an enclosed area protected from dust. The following describes how the user can interface with and control the method of the invention in one embodiment, by using a WINDOWS program on the PC.

Computer Control of Method Parameters

In one embodiment of the invention, the Graphical User Interface (GUI) is performed in a Windows application on a computer. The Graphical User Interface is called up via an icon in the windows environment in which a double click on the mouse activates a Concrete Assurance System Technology program (CAST).

Since CAST is a Windows application it utilizes the Graphical User Interface to allow the user to choose with a "mouse" any of a number of items from a drop down menu in any order. Clicking a button on the mouse selects the features desired as follows.

I. File

Choosing FILE, produces a drop down menu to select from the following modules: new type block, open type block, save, save as, close, preferences, and exit.

A. New Block Type

This module activates another drop menu that allows the user to input the type of block, the number of pallets that have to fail before the alarm is activated, alarm criteria, the specified block height, and the height tolerances reflecting both plus and minus dimensions. This program is flexible enough that one does not have to have the same tolerances for above as well as below and still have the confidence limit within the plus and minus criteria.

B. Open Block Type

This module provides a listing of various block types available as files stored on the hard drive. It also has a list of file types which, if activated, on a downward scroll gives one the block types, text files, old files or one can go to the directories portion which will tell one what is available on the hard drive and another item labeled drives which allows for the ability of going to either A or B floppy drive then C or D hard drive. The section entitled Operational Menus below describes using the Graphical User Interface to control operational parameters.

C. Save

This module allows the user to save the block type and all of the data that has been collected during the time the block type was operational.

D. Save as

This allows the capability of the file to be saved to either the hard drive with another name or the file to be saved to a floppy drive on either the same name or a different name. This feature gives more flexibility than the SAVE module.

E. Close

This module properly closes the application and exits from the CAST application and return to the window's environment.

F. Preferences

This module activates a category from a scroll bar that provides the user a means of customizing the way CAST defaults and or operates in a variety of areas. The areas which may be set are: display, communications, history files, charts, data analysis, or miscellaneous options.

1.) Display preferences: show status bar, use metric units, save window on exit, show multiple messages, process numbers view, show sound velocity, initial view, and save preferences.

a.) Show status bar allows the user to specify whether or not one should show the status bar. The status bar is in the bottom left hand corner and pictorial depiction of the five ultrasonic transducers and whether or not they're passing or failing the immediate measurements of the cinder block. The five circles with the numbers represent the transducers and will darken if a transducer gets a bad measurement and fails the algorithm for pass/fail. Also shown here is the number of pallets in the buffer and which one is in view, the block type and the status of communications or sound velocity.

b.) Use metric units, allows the user to toggle the system between USA standards or metric units.

c.) The save window on exit preference if selected will automatically save the data buffer and block type upon program exit.

d.) The show multiple messages permits the user to stop the system from displaying multiple messages. Multiple messages are featured when one has the same communication errors, it will show it over and over again.

e.) The process numbers view item allows the user to examine the raw data by not converting the ultrasonic echo times to distances.

f.) The show sound velocity is a module that depicts the sensitivity of the program to the speed of sound which is affected by humidity and temperature and quick changes in the environment. Therefore the sound of velocity could change from almost minute to minute in an either very hot or very cold environment and can be monitored by the use of this preference.

g.) The Initial view preference allow the user to define the initial view which CAST will use upon start up and can be set to a 3-D view, a side view, the actual numbers, or an X-bar which plots the test data for each pallet in the buffer in order to indicate trends.

h.) The maximum messages allows for the how many messages one will allow during operation of CAST.

i.) The feature called save preferences in a windows environment ensures that the preestablished preferences will be saved and used the next time the program is utilized.

2. Communications Preferences a.) From the communications preferences category, one can choose which communications port of the PC the system is using.

b.) Configure the port for communications protocol using the ports button.

c.) Auto start communications can also be selected and the system will initiate contact with the conveyor module upon program start up.

d.) This menu also allows the user to disable any of the transducers in the event they are not needed or the unit has failed. If a sensor is disabled, it is totally ignored by both the conveyor module and the PC program.

3. History files preferences consist of: create backups, two level history, prompt for save, history has been modified and auto save.

a.) If selected create backups will automatically copy the history file to a back up file before updating the file.

b.) Selecting two level history will allow the user to view the existing interval as well as a second user definable interval (e.g., last shift). This feature will be helpful in evaluating statistical process control and trend analysis.

c.) Prompt before save will cause the program to request user verification before saving the data upon exit.

d.) History buffer has been modified is a feature that notifies the user that identified errors from the CAST system have been amended (stopping the manufacturing and correcting the problem) and then continued to collect operational data with parameters that have been modified from an earlier time frame.

e.) Auto Save permits the user to set the program to automatically save the history buffer every couple of minutes with the save interval and current interval being user definable (e.g., 8 hours per shift).

4. Charts preferences: permits the user to define the default look of the charts. Specifically the user may define whether axis, grid lines, limit lines, direction arrows, legend (block type and tolerances) are displayed; whether to show out of tolerance points in red, and the zoom percentage of the charts.

5.) Analysis preferences define how the program analyzes the data. These preferences will not be user definable in the final product and are shown for testing purposes only.

6.) Miscellaneous preferences include: enable password protection, enable alarms, suppress warning beeps, use dummy data, sensor time are two way, and consecutive pallets before alarm.

a.) Enabling password protection keeps security for the operation by preventing anybody who does not know the password from tampering with the system settings.

b.) Enabling alarms will permit CAST to send the an alarm after the specified number of pallets fail.

c.) Suppress warning beeps will prevent audible alarms when an error is detected.

d.) Sensor time are two way puts CAST in a developmental diagnostic mode. This option will be removed for production.

e.) Consecutive bad pallets allows the user to define the number of bad pallets required before an alarm is activated.

G. Exit

Exit takes the user out of the window application and back into the program manager.

II. Help

This on-line module is not active in this embodiment, but can provide context sensitive help information.\

Operational Menus

Under normal operations on the plant floor the open block type would be activated providing six mini-windows or child windows. The headings of the first "child window" titled legend shows the user what the tolerances are established , what the confidential level is, what the block height that is activated , and a side view of the readings of the five transducers as the cinder blocks are going through the measurement device of CAST. There are approximately three to five hundred measurements taken within a three second time frame and the PC display provides almost instantaneous readouts that are then compared to the specifications outlined in legend that allows for plus or minus upper confidence level to the preestablished tolerance.

I. Open Block Type

Across these particular tool bar is the element file, control, pallet, chart, view, window and help key.

A. File

To activate, take the mouse and click on the file, one will get the exact same drop down menu as the original File that has already been described.

B. Control

If one activates the control feature, the drop down menu modules are block parameters which displays the block type, the alarm criteria, the history size, the block height, tolerances of confidence level which has already been featured. One toggles the alarm on or off which allows for cutting off either the strobe light or the sound just by clicking the alarm on or off. The module designated clear data asks whether or not one wants to clear all the history data from the pallets. Another item is setup which provides the hardware setup which places the system in a calibration mode. In this mode the system "learns" its environment and calculates parameters which will effect overall system performance. The next module in the drop down menu is test parameters which allows for a view of the pallet time, the height with a plus and minus and how many points were done for each one of the instruments. The last module in control is either the opening or closing of communications between the controller on the operating line and the PC. The measurements that are taken from the ultrasonic transducers are sent to the PC for calculations to be done based on the original parameters setup and communications between these two must be in sync.

C. Pallet

The third item on the menu tool bar called pallet provides the measurement reading of the current pallet or one can go to the previous pallet or go to the next pallet that is downstream. Another module called go to allows one to be specific about any pallet to display. The last module on the drop down menu is called show status that relates the number of transducers, how many measurements are taken on the pallet, the date, the time, whether or not CAST analysis is accepting or rejecting the pallets based on the parameters, how many measured points that it actually processed, and the minimum/average/maximum height and the relative relationship of that height.

D. Chart

If one clicks on another child window, for example, with the heading of any of the transducers one will get another item on the menu bar called chart. The drop down menu on chart is axes, that will put a vertical and horizontal axis for that particular child window. If one activates gridlines it will put down the gridlines in the form of whatever the tolerances were. If one activate the limit lines it will provide the plus and minus confidence levels based on the target height as well as the upper and lower tolerance levels. If one activate the zoom modules it will zoom at where the upper and lower tolerances are which are primarily for the casts systems is at the top of the block that is just currently passed and has been measured. The last module is applied to all that whatever one has activated in this menu will be activated to the other four (4) transducer windows. It will repeat the message more time to ensure that one wants to activate all these changes to the transducers windows.

E. View

The first module of the drop down window is a 3D view of the cinder block. During the operations of manufacturing cinder blocks there can be different blocks configurations on a pallet such as: four 6 inch blocks, three 8 inch blocks, two 10 inch blocks, or two 12 inch blocks. CAST takes the measurements from the five transducers and builds 5 (five) slices of a solid 3D drawing whether or not the configuration is two, three, four or six blocks. This would allow the operator to review whether or not the out of tolerance condition in the manufacturing arena is it sloping front to back or side to side. The module labeled numbers furnishes one the actual measurements that the transducers are processing. All of the numbers are in black except for those measurements that are out of tolerance and they are highlighted in red. The X-bar module plots the average test data for each pallet in the buffer in order to indicate trends and is useful to indicate a system which is slowly going out of tolerance. The status bar is a bar that is across the bottom of the screen. The left bottom portion has been previously described. The five transducers are used to depict bad measurement by turning black. This status bar can also be used to assist the user because the ultrasonic transducer verifies itself to be operating correctly through diagnostic software and will also stay black, thereby, notifying the user that the particular transducer has discontinued operation rather than give bad measurement and by doing so identifies which transducer needs to be replaced. The next block in the bottom status bar gives the count of pallets that are being processed during a particular time; the next block is the file name; the last block across the bottom is the analysis of either accept or reject of the pallet that has just been measured.

F. Window

The window element in the menu tool bar when clicked has the following drop down menus; tile will take the six windows and overlap them on each other. Cascade will put them in one row behind each other serially. Arrange puts the six child windows into what the customer normally sees which is taking the six and putting them side by side so that one can see everything at the same time. Arranging icons is a feature of automatically arranges equal spacing for the icons within the window. The next items 1 through 5 are the headings for the child windows titled transducers 1 to 5 and the sixth heading called legend. One click on any of these will activate that particular child window.

II. Help

This on-line module is not active in this embodiment, but can provide context sensitive help information.

One (copyrighted) version of source code that will allow implementation of the described embodiments of CAST and the above Graphical User Interfaces is provided in Appendix 1 (appendix on microfiche). However, one skilled in computer programming will also be able to write different embodiments of software to accomplish the computer control portion of the method of the invention as disclosed above, without copying the software disclosed in Microfiche Appendix 1. Alternatively, the method of the invention can also be practiced by replacing some functions of the computer software with hard-wired electronic circuits. Parameters and testing criteria may be predefined or selectable by the user using switches or software, as in the above described embodiments.

Cinder Block Measuring Bracket

Returning to FIGS. 1 and 2, a transducer 21 or series of transducers 21a through 21e are provided along the length of track 23 on bracket 2 (any number of transducers may be used in other embodiments). The position of the transducers 21a–21e is adjustable along track 23, so that the transducers will span the entire row of cinder blocks 4 proceeding along the conveyor belt 5. The method of the invention for measuring the cinder blocks is described as follows, with reference to individual transducer 21c (the other transducers are operated similarly).

When no pallet 6 or cinder blocks 4 are positioned beneath the transducer 21, the transducer 21 registers as infinity. As soon as the pallet is detected by the transducer, the software on the microcontroller on the circuit board of the bracket 2 begins the measurement algorithm. First, all flags are reset and whatever software housekeeping is needed is accomplished. When the pallet 6 is first detected, a self-sensing calibration routine is performed to measure the speed of sound at the time the pallet 6 passes beneath the transducer. This is accomplished using an assumed value for the distance between the pallet 6 and the transducer 21c. This value needs to be set only once when the apparatus is first set up. Once this calibration is accomplished, the "height" of the top of the pallet 6 is set as zero. This method allows for use of different pallets of different thicknesses.

After adjusting for the pallet distance, the software waits until the transducer first senses an edge of a cinder block 4. Many (typically over one hundred) such measurements are made on each block. A number of transducer measurements (which number can be defined by the user using the graphical user interface as explained above) at the very edge of the bock are discarded, to eliminate the scatter effect caused by the rough edges of the block. A similar number of transducer measurements at the following edge of the block (immediately preceding detection of the "zero level" pallet) are similarly discarded. The transducer measurements not discarded are entered into a moving average. The number of transducer measurements used for each moving average is variable and may be set by the user.

Assuming the case where five transducer measurements are used for each moving average, and three "edge" measurements are to be discarded to eliminate "scatter effect," the measurement routine proceeds as follows. The first three transducer measurements above zero are discarded. The next five transducer measurements are averaged to produce one height measurement "point." These points are used for the graphical display and other testing routines. When the next transducer measurement is received, it is averaged into the moving average while at the same time the earliest transducer measurement being used for the moving average is removed from the moving average. For example, suppose the first ten "above zero" transducer measurements of height h(1) through h(10) of the block 4 following the "zero level" pallet measurement are received. Measurements h(1)–h(3) are discarded to eliminate scatter effect. Then, transducer measurements h(4)–h(8) are averaged together to produce a moving average. This moving average is used as the first height measurement point. Then, one-fifth of transducer measurement h(4) is subtracted, and one-fifth of transducer measurement h(9) is added to the moving average, to produce the next height measurement point. This process continues until the "zero level" pallet 6 is again detected, at which time the final three height measurement points are discarded to eliminate or reduce the scatter effect.

In one embodiment of the invention, the above algorithm is controlled be a microprocessor or controller 12 connected to one or more signal generators 11 and transducers 21. One (copyrighted) version of source code for a computer program that will run in the microprocessor or controller 12, a functional chart, and module description of the software, are provided in Microfiche Appendix 2. However, one skilled in computer programming will also be able to write different embodiments of software to accomplish the algorithm without copying the software disclosed in Microfiche Appendix 2. Alternatively, the method of the invention can also be practiced by replacing functions of the computer software with hard-wired electronic circuits.

As illustrated in FIG. 1, communication is established between computer 1, bracket 2 with microcontroller or circuit board, and the panel assembly 8 with panel box 3 and alarm or warning device 7.

The computer 1 in one embodiment is an IBM PC compatible personal computer with INTEL 486 chip, but any suitable computer can be used.

The bracket 2 is divided into two sections. The upper section houses the electronic assembly comprising a controller circuit card or controller 12 and a signal generator 11. The housing is designed to be waterproof so that the bracket can be washed off with a water hose, resistant to electromagnetic interference (EMI), and designed to block out high external noise levels. The lower section of the bracket not only supports the upper subassembly section but allows for the maximum amount of transducer movement flexibility depending upon the block configuration being manufactured. Bottom flanges on the lower section of the bracket can be designed to prevent the transducers from being damaged in case of pallet kickback. An interior housing in the upper bracket section holds the microcontroller or controller circuit card 12 and five signal generator modules.

Power Panel Assembly

A third element of the CAST system is the power panel assembly 8 including panel box 3 and strobe light or other alarm 7. In the manufacturing of cinder blocks, there is usually a very high noise level (over 125 db) in the environ and persons in the area wear earplugs. If the CAST system identifies a metrology problem, an visual alarm can notify everyone in that area via the strobe light 7. The strobe 7 light is powered at and is physically attached to the panel box 3. The panel assembly 8 can be designed for resistance to electromagnetic interference (EMI), to operate in a dirty environment, and to be capable of being washed down with a water hose.

Figure 2:
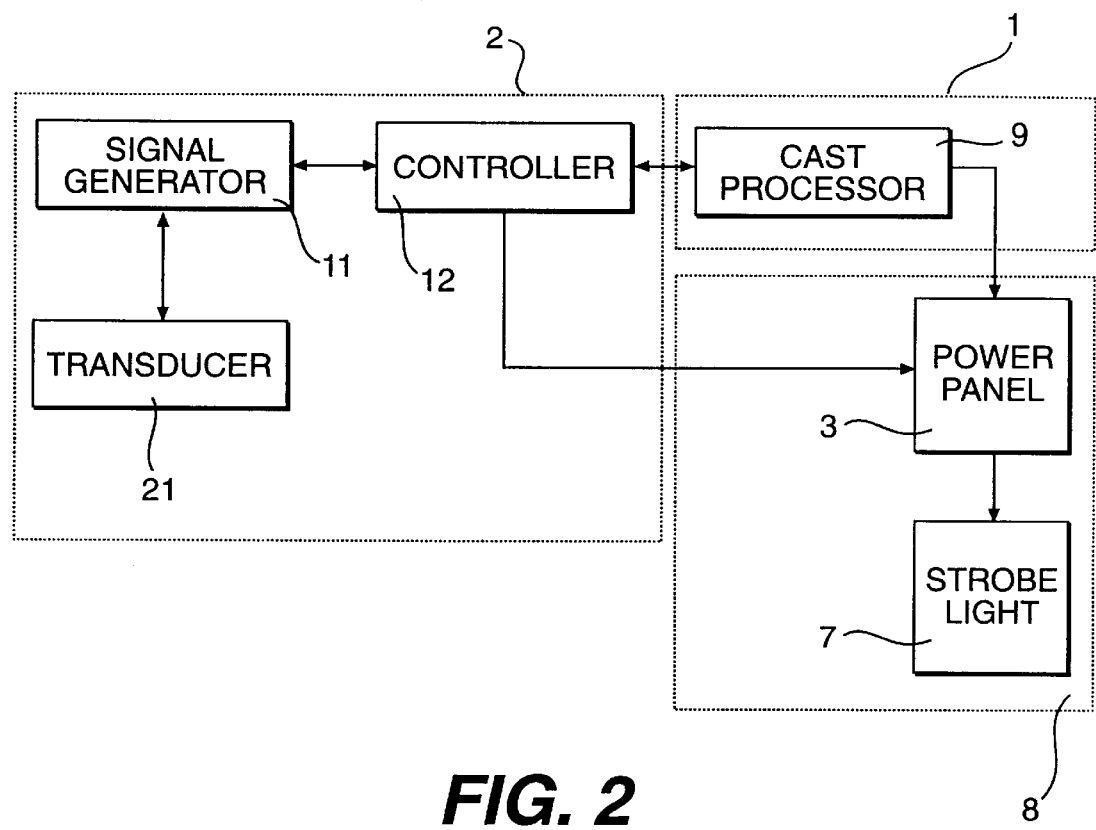
FIG. 2 is a functional diagram of the components of the apparatus of the invention and the data flow therebetween.
Figure 3:
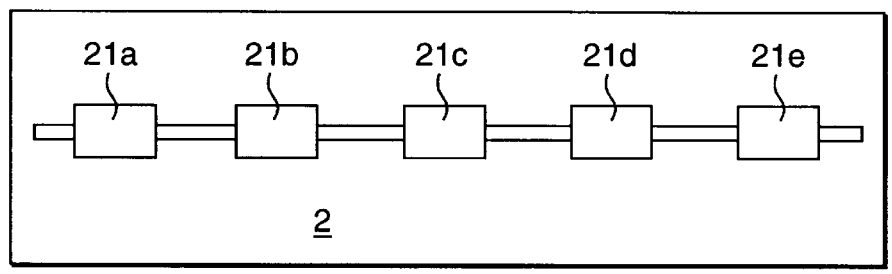
FIG. 3 is a bottom view representation of an embodiment of the bracket section of the apparatus of the invention.

In one embodiment of the invention, with reference to FIG. 2, the CAST processor 9 of the computer 1 can enable and disable the strobe light or other alarms 7, controls the parameters used by the controller 12, and receives and processes observed measurement data for display. The controller 12 controls the signal generators 11 and transducers 21 as described above, sends status and observed data to the processor 9, and sends alarm and any needed flag signals to the power panel box 3 and strobe light 7.

Engineering drawings for one embodiment of the apparatus of the invention, and further description of the interaction between the different parts thereof, are provided in Microfiche Appendix 3.

While the present invention has been particularly shown and described with reference to the preferred mode as illustrated in the drawing, it will be understood by one skilled in the art that various changes in detail may be effected therein without departing from the spirit and scope of the invention as defined by the claims.

What is claimed and desired to be secured by United States Letters Patent is:

1. In a computer-based system comprising: a CPU, an input means connected to the CPU, a memory means associated with the CPU, a data transmission means connecting the CPU, a controller card connected to the data transmission means, an ultrasound transducing means connected to the controller card, a timing device connected to the controller card, a memory means associated with the controller card, a feedback device connected to the controller card, and an environmental adaptation means, a method of providing feedback regarding tolerance for a dimension of a concrete block in relation to a datum, comprising the steps of:

a. the input means obtaining, and the CPU storing as data in the CPU memory means, a datum defining a certain distance from the ultrasound transducing means;

b. the input means obtaining, and the CPU storing in the CPU memory means, data defining a range of tolerance within which a dimension of the concrete block may vary from the datum;

c. the CPU calculating, and storing as data in the CPU memory means, speed of sound in the environment of the system;

d. the ultrasound transducing means propagating an ultrasonic wave toward the concrete block;

e. the ultrasound transducing means detecting a reflection of the ultrasonic wave off the concrete block;

f. the timing device measuring, and the controller card storing as data in the controller card memory means, time elapsing between propagation of the ultrasonic wave and detection of the reflection of the ultrasonic wave;

g. the controller card determining, and storing as data in the controller card memory means, a fraction of the time elapsing proportionate to time accruing between propagation of the ultrasonic wave and the wave striking the concrete block by retrieving the elapsed time data and applying a fractioning function;

h. the controller card retrieving the fractional elapsed time data, the data transmission means transmitting the fractional elapsed time data to the CPU, and the CPU storing as data the fractional elapsed time data in the CPU memory means;

i. the CPU determining, and storing as data in the CPU memory means, a distance between the ultrasound transducing means and the concrete block by retrieving the fractional elapsed time data from the CPU memory means and applying a conversion function to said fractional elapsed time data, said conversion function retrieving from the CPU memory means, and utilizing, the speed of sound data;

j. the CPU determining, and storing as data in the CPU memory means, an actual dimensional distance between the concrete block and the datum by retrieving data pertaining to the distance between the ultrasound transducing means and the concrete block, retrieving the datum data, applying a difference function, storing the actual dimensional distance as data in the CPU memory means in a data series, and reducing error wherein one or more actual dimensional distance data of a distance determination made in proximity to an edge of the block is discarded from the data series;

k. the CPU determining whether the distance between the concrete block and the datum is within the tolerance range by retrieving the tolerance range data and the actual dimensional distance data from the CPU memory means and applying a comparison function;

l. the feedback device outputting feedback in response to the applying of the comparison function;

m. performing the following steps a plurality of times:

(i) the CPU calculating, and storing as data in the CPU memory means, speed of sound in the environment of the system;

(ii) the ultrasound transducing means propagating an ultrasonic wave toward the concrete block;

(iii) the ultrasound transducing means detecting a reflection of the ultrasonic wave off the concrete block;

(iv) the timing device measuring, and the controller card storing as data in the controller card memory means, time elapsing between propagation of the ultrasonic wave and detection of the reflection of the ultrasonic wave;

(v) the controller card determining, and storing as data in the controller card memory means, a fraction of the time elapsing proportionate to time accruing between propagation of the ultrasonic wave and the wave striking the concrete block by retrieving the elapsed time data and applying a fractioning function;

(vi) the controller card retrieving the fractional elapsed time data, the data transmission means transmitting the fractional elapsed time data to the CPU, and the CPU storing as data the fractional elapsed time data in the CPU memory means;

(vii) the CPU determining, and storing as data in the CPU memory means, a distance between the ultrasound transducing means and the concrete block by retrieving the fractional elapsed time data from the CPU memory means and applying a conversion function to the fractional elapsed time data, said conversion function retrieving from the CPU memory means, and utilizing, the speed of sound data;

(viii) the CPU determining, and storing as data in the CPU memory means, an actual dimensional distance between the concrete block and the datum by retrieving the data pertaining to the distance between the ultrasound transducing means and the concrete block, retrieving the datum data, and applying a difference function;

(ix) the CPU determining whether the distance between the concrete block and the datum is within the tolerance range by retrieving the tolerance range data and the actual dimensional distance data from the CPU memory means and applying a comparison function;

(x) the feedback device outputting feedback in response to the applying of the comparison function.

2. The feedback providing method of claim 1 wherein the number of actual dimensional distance data discarded is three.

3. The feedback providing method of claim 2 further comprising the steps of:

a. retrieving in a serial fashion, and storing in a segregated data means of the CPU memory means having at least one data position, a first data position and a last data position, a consecutive plurality of actual dimensional distance data from the data series;

b. applying, and storing as data in the CPU memory means, a data averaging function to the segregated data means;

c. repeating the following steps while any actual dimensional distance data remain in the data series:

(i) discarding the data in the first position of the segregated data means, and advancing the position of each remaining data within the segregated data means;

(ii) retrieving in a serial fashion, and storing in the last data position of the segregated data means, dimensional distance data next occurring in the data series;

(iii) applying the data averaging function to the segregated data means and storing the result as data in the CPU memory means.

4. The feedback providing method of claim 3 wherein the number of data positions of the segregated data means is five.

5. The feedback providing method of claim 3 wherein the step of outputting feedback comprises indicating whether or not the distance between the averaged distance and the datum is within the tolerance range.

6. An environmentally adaptable computer-based apparatus utilizing ultrasound for providing feedback regarding the dimensional quality of concrete blocks positioned on pallets traveling on a conveyor, said apparatus comprising:

a. a first memory means for controlling a CPU;
b. an input means for:
   (i) obtaining, and storing as data in the first memory means, a datum defining a certain distance from an ultrasound transducing means;
   (ii) obtaining, and storing as data in the first memory means, a range of tolerance within which a dimension of the concrete block may vary from the datum;
c. an ultrasound transducing means for:
   (i) propagating an ultrasonic wave toward the concrete block;
   (ii) detecting a reflection of the ultrasonic wave off the concrete block;
d. a timing device for measuring an amount of time elapsing between propagation of the ultrasonic wave and detection of the reflection of the ultrasonic wave;
e. a second memory means for controlling a controller card and for storing as data elapsed time measured by the timing device;
f. a controller card, connected to the ultrasound transducing means, the timing device and the second memory means, said controller card adapted to determine, a plurality of times, a fraction of the elapsed time proportionate to time accruing between propagation of the ultrasonic wave and the wave striking the concrete block by retrieving the elapsed time data and applying a fractioning function as well as store as data actual dimensional distances in the first memory means in a series;
g. a data transmission means for transmitting the fractional elapsed time data to the CPU;
h. a CPU, associated with the first memory means, adapted to:
   (i) receive, and store in the first memory means, the fractional elapsed time data;
   (ii) calculate, and store as data in the first memory means, the speed of sound in the environment of the apparatus;
   (iii) determine, and store as data in the first memory means, a distance between the ultrasound transducing means and the concrete block by retrieving the fractional elapsed time data from the first memory means and applying a conversion function to the fractional elapsed time data, said conversion function retrieving from the first memory means, and utilizing, the speed of sound data;
   (iv) determine, and store as data in the first memory means, an actual dimensional distance between the concrete block and the datum by retrieving the data pertaining to the distance between the ultrasound transducing means and the concrete block, retrieving the datum data, and applying a difference function;
   (v) determine whether the distance between the concrete block and the datum is within the tolerance range by retrieving the tolerance range data and the actual dimensional distance data from the first memory means and applying a comparison function;
   (vi) perform a plurality of times those tasks for which said CPU has been adapted;
   (vii) store as data actual dimensional distances in the first memory means in a series;
   (viii) reduce error by discarding from the data series one or more actual dimensional distance data of a distance determination made in proximity to an edge of the block;
i. a feedback device for outputting feedback responsive to the applying of the comparison function.

7. The apparatus of claim 6 wherein the number of actual dimensional distance data discarded is three.

8. The apparatus of claim 6 wherein said CPU is adapted to:
a. retrieve in a serial fashion, and store in a segregated data means of the CPU memory means having at least one data position, a first data position and a last data position, a consecutive plurality of actual dimensional distance data from the data series;
b. apply, and store as data in the CPU memory means, a data averaging function to the segregated data means;
c. repeat the following steps while any actual dimensional distance data remain in the data series:
   (i) discard the data in the first position of the segregated data means, and advance the position of each remaining data within the segregated data means;
   (ii) retrieve in a serial fashion, and store in the last data position of the segregated data means, dimensional distance data next occurring in the data series;
   (iii) apply the data averaging function to the segregated data means and store the result as data in the CPU memory means.

9. The apparatus of claim 8 wherein the number of data positions of the segregated data means is five.

10. The apparatus of claim 9 wherein the feedback device comprises an indicator for indicating whether or not the distance between the averaged distance and the datum is within the tolerance range.

* * * * *